(12) United States Patent
Klettke et al.

(10) Patent No.: US 8,142,562 B2
(45) Date of Patent: Mar. 27, 2012

(54) CURABLE DENTAL RETRACTION COMPOSITION, METHOD OF PRODUCTION AND USE THEREOF

(75) Inventors: Thomas Klettke, Diessen (DE); Ruediger Hampe, Wörthsee (DE)

(73) Assignee: 3M Innovative Properties Company, Saint Paul, MN (US)

( * ) Notice: Subject to any disclaimer, the term of this patent is extended or adjusted under 35 U.S.C. 154(b) by 522 days.

(21) Appl. No.: 12/376,527

(22) PCT Filed: Aug. 2, 2007

(86) PCT No.: PCT/US2007/075065
§ 371 (c)(1),
(2), (4) Date: Feb. 5, 2009

(87) PCT Pub. No.: WO2008/021740
PCT Pub. Date: Feb. 21, 2008

(65) Prior Publication Data
US 2010/0183999 A1    Jul. 22, 2010

(30) Foreign Application Priority Data
Aug. 8, 2006 (EP) .................................. 06016477

(51) Int. Cl.
*A61K 6/097* (2006.01)
(52) U.S. Cl. .......... 106/35; 433/229; 433/224; 433/215; 523/105; 514/769; 514/779
(58) Field of Classification Search .................. 106/35; 433/229, 224, 215; 523/105; 514/769, 779
See application file for complete search history.

(56) References Cited

U.S. PATENT DOCUMENTS

| | | | |
|---|---|---|---|
| 4,381,947 A * | 5/1983 | Pellico | ....... 106/38.51 |
| 4,522,593 A | 6/1985 | Fischer | |
| 4,674,661 A | 6/1987 | Herold | |
| 4,857,331 A * | 8/1989 | Shaw et al. | ....... 424/440 |
| 4,890,931 A | 1/1990 | Herold | |
| 5,167,448 A | 12/1992 | Herold | |
| 5,362,495 A | 11/1994 | Lesage | |
| 5,596,084 A * | 1/1997 | Sanderson et al. | ....... 536/3 |
| 6,170,714 B1 | 1/2001 | Lesage | |
| 6,383,279 B1 | 5/2002 | Eckhardt | |
| 6,715,645 B2 | 4/2004 | Peuker | |
| 6,872,387 B1 | 3/2005 | Ma | |
| 2002/0058725 A1 | 5/2002 | Watanabe | |
| 2002/0156149 A1 | 10/2002 | Schaub | |
| 2004/0106086 A1 | 6/2004 | Dragan | |
| 2005/0008583 A1 | 1/2005 | White | |
| 2005/0069838 A1 | 3/2005 | Kollefrath | |
| 2005/0250871 A1 | 11/2005 | Bublewitz | |
| 2005/0260543 A1 | 11/2005 | Dragan | |
| 2005/0287494 A1 | 12/2005 | Yang | |
| 2007/0154556 A1 | 7/2007 | Xu | |

FOREIGN PATENT DOCUMENTS

| | | |
|---|---|---|
| DE | 3736155 | 5/1989 |
| EP | 1577227 | 9/2005 |
| EP | 1611876 | 1/2006 |
| EP | 1 707 178 A1 | 10/2006 |
| EP | 1741405 | 1/2007 |
| EP | 1759657 | 3/2007 |
| GB | 2 090 272 A | 7/1982 |
| JP | 2006/056833 | 3/2006 |
| WO | WO 90/15587 | 12/1990 |
| WO | WO 96/25915 | 8/1996 |
| WO | WO 96/27342 | 9/1996 |
| WO | WO 98/28090 | 7/1998 |
| WO | WO 2005/007095 | 1/2005 |
| WO | WO 2005/016170 | 2/2005 |
| WO | WO 2005/016783 | 2/2005 |
| WO | WO 2005/084819 | 9/2005 |
| WO | WO 2005/094714 | 10/2005 |
| WO | WO 2005/118154 | 12/2005 |
| WO | WO 2006/007780 | 1/2006 |

OTHER PUBLICATIONS

Drury, "The Tensile Properties of Alginate Hydrogels", Biomaterials, 2004, vol. 25, pp. 3187-3199.
Ferrari, "Tissue Management with a New Gingival Retraction Material: A Preliminary Clinical Report", Journal of Prosthetic Dentistry, 1996, vol. 75, No. 3, pp. 242-247.
Kuo, "Ionically Crosslinked Alginate Hydrogels as Scaffolds for Tissue Engineering: Part 1. Structure, Gelation Rate and Mechanical Properties", Biomaterials, 2001, vol. 22, pp. 511-521.
Laforgia, "Cordless Tissue Retraction for Impressions for Fixed Prosthesis", Journal of Prosthetic Dentistry, Apr. 1967, vol. 17, No. 4, p. 379-386.
Moresi, "Viscoelastic Properties of Microbial Alginate Gels by Oscillatory Dynamic Tests", Journal of Food Engineering, 2004, vol. 64, pp. 179-186.
European Search and Partial Search Reports for EP Application No. 06016477, 12 pgs.
Written Opinion for PCT/US2007/075065, 7 pages.
International Search Report for PCT/US2007/075065, 6 pages.
Marburger, "Alginate in der Medizin," *Chemie und Medizin*, Jul. 15, 2002; 5(51):27-35. English translation of Sections 2.2, 3.1.1., and 3.2.2 included.

* cited by examiner

*Primary Examiner* — Carol M Koslow
(74) *Attorney, Agent, or Firm* — Pamela L. Stewart

(57) ABSTRACT

The invention relates to a curable dental retraction composition for reacting gingiva from a prepared tooth structure. The composition comprises an alginate, a di- and/or trivalent ion source, water, a retarder and a filler.

15 Claims, 2 Drawing Sheets

CURABLE DENTAL RETRACTION COMPOSITION, METHOD OF PRODUCTION AND USE THEREOF

CROSS REFERENCE TO RELATED APPLICATIONS

Figure 1:
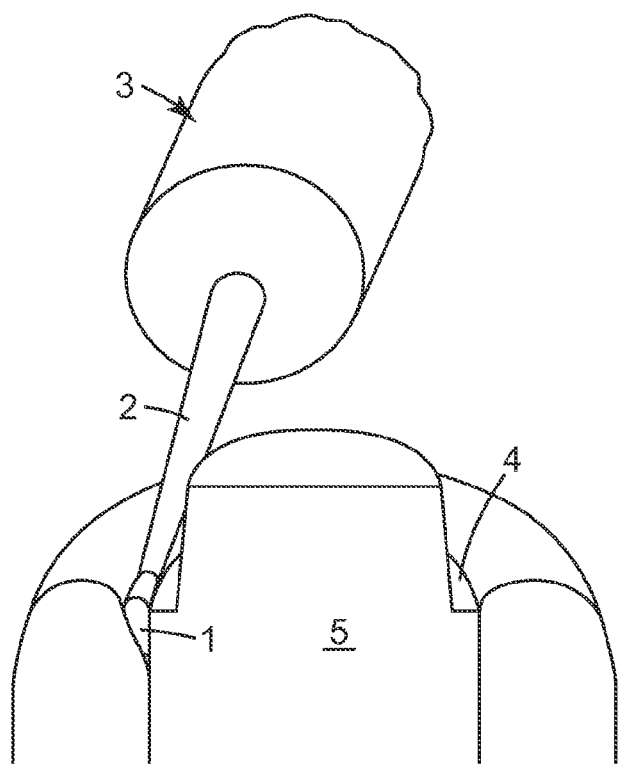

This application is a national stage filing under 35 U.S.C. 371 of PCT/US2007/075065, filed Aug. 2, 2007, which claims priority to EP Application No. 06016477.9, filed Aug. 8, 2006, the disclosures of which are incorporated by reference in their entirety herein.

FIELD OF THE INVENTION

The invention relates to the curable dental retraction composition and its use for retracting the gingiva from a prepared tooth structure.

BACKGROUND OF THE INVENTION

For retracting gingiva from a prepared tooth a cord can be used. In this respect, a retraction cord is packed between gingival tissue and the margin of the prepared tooth using an appropriate dental instrument e.g. a Heinemann spatula. To obtain sufficient vertical and horizontal retraction of gingival tissue, it is often necessary to pack several lengths of retraction cord into the sulcus in order to be able to make a detailed dental impression. A description of the background in regard to retraction cords can be found e.g. in U.S. Pat. No. 4,522,593.

Generally, dental retraction cords are sometimes difficult to place into the gingival sulcus. The procedure can also be time consuming. It can also be cumbersome to remove the retraction cord prior to taking the impression. Coagulated blood may adhere to the cord and removing it may open the wound again which results in bleeding.

For a more convenient placement retraction pastes have been suggested.

US 2005/0287494 and EP 1 611 876 A1 describe non-hardening pastes with a defined viscosity containing fibrillated fibers, filler(s), adstingent(s) and water.

U.S. Pat. No. 5,362,495 describes an injectable non-hardening paste. The paste can be delivered with a application device described in U.S. Pat. No. 6,170,714.

US 2004/0106086 describes an impression material that is used for retraction of gingival tissue.

US 2005/0260543 describes silicone based materials in which astringents are incorporated. This material is essentially used in a two-step technique. A two step technique in which two types of material applied and hardened subsequently in the patients mouth is time consuming for both dentist and patient. A two-step procedure is also uncomfortable for the patient.

WO 2006/007780 refers to a biologically activated injection bone reconstruction gel. It is stated that this material can be applicable in fractures, slow healing fractures, bone defects reconstruction, orthopedic surgery and dental diseases. The material is prepared from two components, wherein water is used as a main ingredient. The concentration of alginate in the aqueous composition is within a range of 1 to 4%.

US 2005/0069838 discloses a dental kit and method for retraction sulcus using an expanding silicone compound or mixture of different silicone compounds. However, silicone compounds are inorganic and hydrophobic nature, thus having limited biocompatibility with oral tissue and disadvantages in flowing to moist tissue and tooth surfaces and moist areas like the gingival sulcus.

Dental alginate impression materials are usually delivered in a powdery form which can form an irreversible hydrocolloide in the presence of water. The powder usually contains potassium or sodium alginic acid, filler(s), retarder(s) and additives. The pastes are made either by hand-mixing the powder and water or by using special mixing devices. All dental alginate impression materials usually have a high filler content (generally above about 60 wt. -% with respect to the whole composition in dry form, that is, before water is added). Despite of this high filler content the impression materials have limited tensile strength because of their gel-like consistency after curing and thus are not suitable for use as a retraction material.

A commercially available retraction composition is sold under the name Expasyl™. According to the instruction of use, the viscosity of the composition changes when water is absorbed. However, a reduction in viscosity is sometimes undesirable since having high consistency is one pre-requisite for applying force onto the gingiva for sufficient retraction.

Known retraction devices are often not biocompatible and can thus be tissue irritating.

A further general disadvantage of commercially available pastes used for dental retraction is that the paste cannot be placed cord-like into the gingival sulcus having the result that sometimes the whole prepared tooth is covered with the paste. This prevents pushing the paste deeper into the gingival sulcus using a dental tool like a spatula.

In general, removing of non-hardening pastes before taking the impression is not optimal. Usually it is rinsed off with water. During this procedure there is a risk that residues of paste may remain in the sulcus. These residues may prevent the impression material from flowing into the sulcus area and may negatively influence the setting of the impression material which is applied subsequently. After rinsing off the paste with water and additional drying step is required before the impression can be taken.

Hardening materials are easier to remove. However, they are not very hydrophilic. This might cause problems in regard to flowability of the material into the gingival sulcus.

Therefore, a hydrophilic curable paste would be desirable.

Thus, it is an object of the invention to provide a paste which can be used for retraction of oral tissue especially prior to impression taking. Ideally, the paste cures in the patient's mouth in a reasonable amount of time.

SUMMARY OF THE INVENTION

In order to at least partially address at least one of the problems mentioned above, the invention provides a curable composition for retracting ginigva from a tooth structure comprising an alginate as component A,
a di- or trivalent ion source as component B,
water in an amount less than about 60 wt. -% as component C,
a retarder as component D,
a filler in an amount less than about 30 wt. -% as component E, wherein the wt. -% are calculated with respect to the whole composition.

In a preferred embodiment the shear storus modulus value $G'_{max}$ of this composition is at least about 150,000 Pa measured with a dynamic stress rheometer equipped with a 15 mm parallel plate geometry with grooved surfaces and a measurement gap of 1 mm at 36° C.

The invention also relates to a kit of parts for producing a composition for retracting gingiva from a tooth comprising part I and Part II, part I comprising water and part II comprising the retarder of the composition, wherein the other components of the composition are either present in part I or in part II or in part I and in part II.

In another embodiment the invention is directed to a kit of parts comprising a curable composition as defined in the text of the invention and a curable impression material, the setting behaviour of which is not negatively affected if cured in the presence of the retraction device.

In a further aspect, the invention relates to a method of producing a curable dental retraction composition, comprising the step of mixing the components of the composition.

In a further aspect, the invention relates to a device for mixing and delivering the curable composition.

Furthermore, the invention relates to a method of using the curable composition comprising the steps of a) providing the curable composition, b) applying the curable composition to a surface.

The invention also relates to a method of using a component with D-glucono-δ-lactone structure for producing a curable dental retraction composition.

Figure 2:
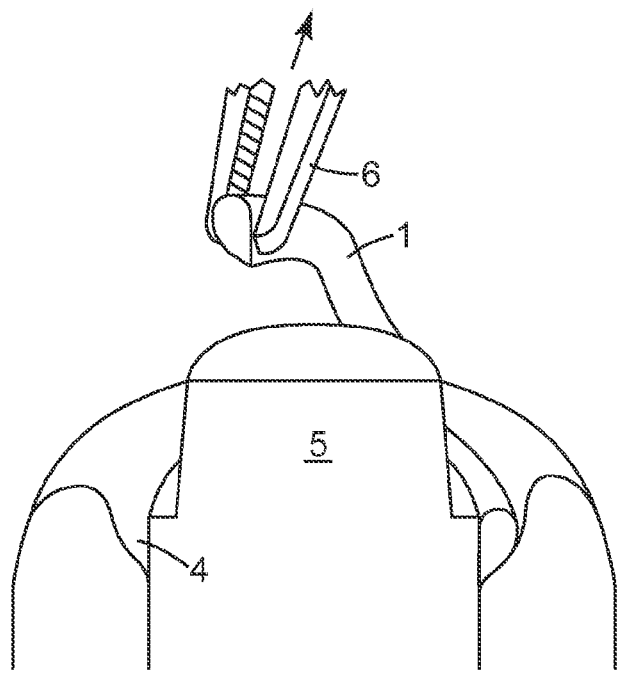
Figure 3:
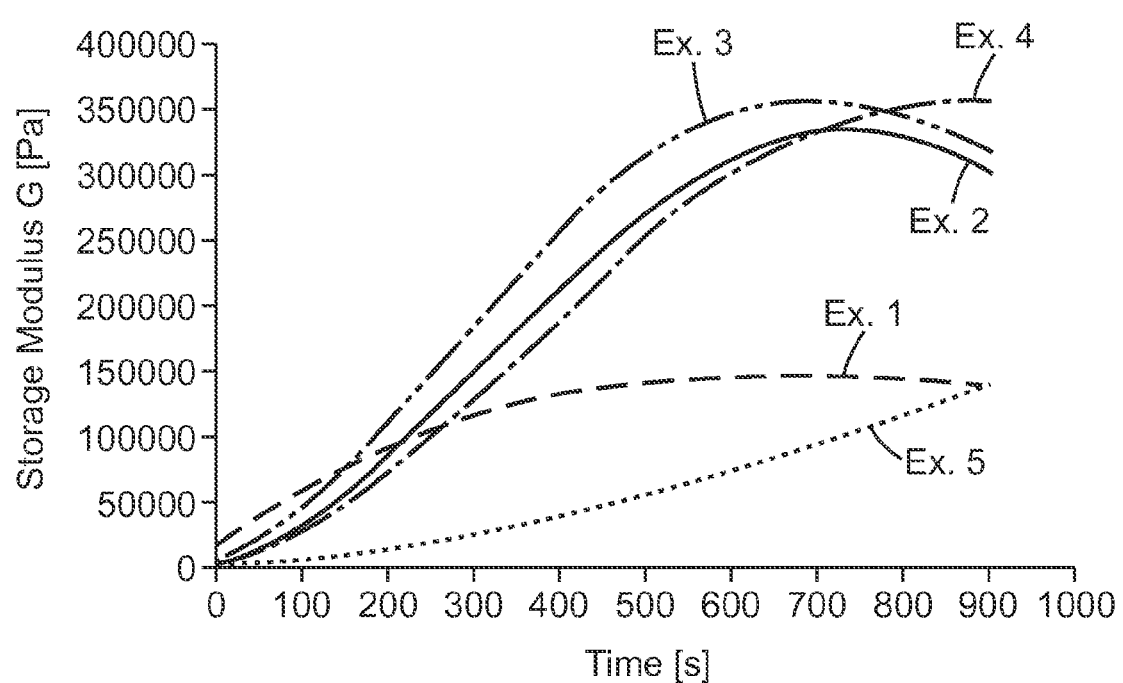

FIGS. 1 and 2 show an embodiment how the curable composition can be applied. FIG. 3 shows the setting reaction of embodiments according to the invention in comparison with reference examples.

DEFINITIONS

A curable composition within the meaning of the invention is a composition which hardens within a reasonable time (e.g. within a couple of minutes, such as about 1 to 30 min or within about 2 to about 10 min) as soon as the curing process has been started. Curing can be achieved at ambient conditions, (e.g. about 20 to about 40° C.) without applying external heat.

In the context of the present invention, a "composition" is understood to be a mixture of two or more components.

The terms "hardening", "setting", "curing" or "curable" are used interchangeable, both referring to the formation of material with a higher molecular weight, by creating a network due to chemical and/or physical interaction.

An alginate within the meaning of the invention is a salt of an alginic acid, Alginates are used for making dental impressions since many years. Alginates are usually delivered as powders and form an irreversible hydrocolloide in the presence of water. The alginic acid is a bio-copolymer containing dehydro-D-mannuronic acid and dehydro-L-guluronic acid. A comprehensive review on alginates used in the dental filed can be found in Chemie and Medizin 2002, pages 27 to 35. Alginate containing materials are preferred as these materials are biodegradable and thus lower the risk of infection during and after the treatment should material remain in the sulcus.

It has been found that alginates show a good flowability of paste into sulcus. This might be due to their hydrophilic nature.

The composition of the invention differs from alginate composition used for making impressions in various aspects. The mechanical properties of the inventive composition are better, e.g. with respect to shear storus modulus value G' or $G'_{max}$, respectively. Moreover, the inventive composition contains less filler and less water compared to common alginate impression materials.

The shear storus modulus value G' or $G'_{max}$, can be determined using an oscillating rheometer. A general description of the measuring method can be found in Journal of Food Engineering 64, 2004, 179-186.

A divalent or trivalent ion source within the meaning of the invention is a component or composition which is able to provide ions with a charge of plus two or plus three if dissolved in a liquid such as water. That is, the divalent ion source is able to dissociate into cations having a charge of plus two (2+) or plus three (3+) and anions over a certain amount over the time.

A retarder within the meaning of the invention is a substance or composition which is able to influence, especially delay the setting of a curable composition. With regard to alginates this can be achieved e.g. by a substance or composition which can influence the availability of cations needed for the setting reaction. In one embodiment, the retarder may undergo a chemical reaction with the cations provided by the di- or trivalent ion source to control the amount of cations capable of reacting with the alginate. In another embodiment, the retarder may alter the solubility of the di- or trivalent ion source. This may have an influence on the concentration of the di- or trivalent ions capable of reacting or interacting with the alginate. The retarder can be of predominantly organic or inorganic nature. The retarder can be water soluble of water insoluble.

A sigmoid function within the meaning of the invention is a mathematical function that produces a sigmoid curve—a curve having an "S" shape. Usually, a sigmoid function follows the logistic function $P(t)=1/(1+e^{-1})$.

In general, a sigmoid function is real-valued and differentiable, having a non-negative or non-positive first derivative, one local minimum, and one local maximum.

If not otherwise indicated molecular weight within the meaning of the invention always means Mw (weight average of the molecular weight) and can be determined for the individual classes of polymers by gel permeation chromatography (GPC) against a standard of defined molecular weight. Suitable measurement methods are known to the person skilled in the art.

The molecular weight of alginates is usually determined by measurement of the viscosity of a defined solution with respect to a calibration curve. The molecular weight of alginates referred to in the invention is based on the information provided by the suppliers.

Network building component within the meaning of the invention are components which are able to form a network by crosslinking reaction between the respective components. This network can be an interpenetrating network, that is a network that interferes with the alginate network or it can be a network that exists besides the alginate network without interference.

A tooth structure within the meaning of the invention is any tooth structure, prepared or ready for preparation by the dentist. It can be a single tooth or two or more teeth.

A haemostic agent within the meaning of the invention is an agent which is able to reduce bleeding to a certain about and/or causes blood to coagulate.

The term "essentially does not" within the meaning of the invention is to be understood that a certain—sometimes unavoidable—effect does usually not take place or only occurs to a minimum amount, wherein the effect does not negatively affect the overall result to be achieved.

The setting behaviour of a curable composition is "not negatively affected" within the meaning of the invention, if the setting of the curable composition takes place within the given specification. Small deviations (e.g. within a range of about 5 to 10%) of physical parameters like Shore hardness, viscosity, working time or setting time, which might occur if e.g. an additive is added or setting takes place in conjunction with other materials or substances (e.g. in the presence of a retraction device or curable retraction composition), are not considered detrimental.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION OF THE INVENTION

Depending on the formulation chosen, the curable composition according to the invention fulfils at least one of the following features:
a) The composition is biocompatible, b) the composition is provided in pasty form, c) the composition has a low water content, d) it might also have a low filler content, e) the composition has a sufficient tensile strength and f) it cures in an appropriate time to be used in the dental field.

It has been found that the inventive curable composition after setting can generally be removed more easily from the sulcus compared to non-hydrophilc compositions. In contrast to the state of the art cords, the cured composition has typically a smooth surface which facilitates easy removal. Because of its smooth surface it may also prevent sticking to coagulated blood which often may cause wound opening and bleeding upon removal.

It can be advantageous if the setting of the curable composition, which usually takes place in the moist environment of an oral cavity, is not negatively influenced by fluids (e.g. saliva or blood or mixture of both) that might be present. In another embodiment, the curable composition can contribute to stop bleeding which might occur when preparing a tooth structure. It has been found that astringents—if desired—can be incorporated into the formulation homogeneously. It has also been found that the inventive curable composition itself has some haemostatic properties due to the presence of multivalent cations that may facilitate blood coagulation. After removal of the cured composition, the rinsing step may be omitted which reduces the risk of opening wounded tissue with a water beam used for rinsing or with an air beam used for drying the treated tissue prior to impression taking. This can contribute to a safe and less time consuming procedure.

In one embodiment, the alginate can be present in the curable composition in an amount of at least about 4 or of at least about 5 or of at least about 8 wt. -% with respect to the whole composition. There is no fixed upper limit for the amount of alginate. However, in a typical embodiment the alginate can be present in the composition up to an amount of about 8 or up to about 12 or up to about 18 wt. -% or up to about 20 wt. -% with respect to the whole composition. Thus, useful ranges for the alginate to be used include ranges from about 4 wt. -% to about 18 wt. -% or from about 4 wt. -% to about 12 wt. -% or from about 8 wt. -% to about 18 wt. -%.

The molecular weight (Mw) of the alginate is not particularly limited, but is usually in the range between about 200,000 and about 400,000 g/mol or between about 250,000 and about 350,000 g/mol or between about 200,000 and about 300,000 g/mol.

The alginate can have a low particle size. An averaged particle size (d90/μm—that is, in 90% of the analyzed volume, the particles have a size below x μm) up to about 200 μm or up to about 75 μm was found to be useful. The particle size can be determined as outlined below.

The particle size can be measured using a Malvern Mastersizer 2000 (Malvern Instruments, Malvern Worcestershire, UK) light scattering instrument. The Mastersizer 2000 uses an integrated optical system to cover the range from 0.02 to 2000 μm. The mixtures to be analyzed are added to the test chamber filled with isopropanol until an obscuration of approximately 8-15% is reached. No ultrasound is applied in order not to alter the particle size distributions. The raw data is processed with the instrument software using a refractive index of 1.459 and applying the Mie correction together with the Fraunhofer approximation, frequently used techniques known to the expert.

The chemical nature of the alginate is not particularly limited, either, however, the alginates which can be used are usually bio-copolymers containing dehydro-D-mannuronic acid and dehydro-L-guluronic acid. Naturally available hydrogel based materials are preferred. Suitable alginates include alginates from algae. Preferred are alginates from algae *Laminaria hyperborea*. Especially useful are alginates from *Laminaria hyperborea* Steam and from *Lessonia trabeculata*. Also synthetic alginates having a high guluronate content can be used. Preferred salts of these alginic acids are sodium and potassium salts. Especially preferred is the potassium salt.

A particularly preferred class of alginates found to be useful for the present invention has a high guluronate content. It was found that alginates with a high content of guluronan units can form stronger gels than those with low guluronan content. A strong gel formation can be advantageous for producing compositions to be used for dental retraction.

The guluronate content of the alginates used can be above about 50 wt. -% or above about 55 wt. -% or even above about 60 wt. -% with respect to the weight of the alginate in dry form. The guluronate content of the alginate can be as high as about 80 wt. -% or about 75 wt. -% with respect to the weight of the alginate in dry form. Ranges which have been found to be useful include between about 50 to about 80 wt. -% or between about 60 and about 75 wt. -% with respect to the weight of the alginate in dry form.

The di- or trivalent ion source can be present in the composition in an amount of at least about 5 or at least about 8 or of at least about 12 or of at least about 15 wt. -% with respect to the whole composition. The divalent ion source can be present in the composition in an amount up to about 5 or up to about 40 or up to about 50 wt. -% with respect to the whole composition. Ranges which have been found to be useful include from about 5 to about 40 or from about 8 to about 50 or from about 12 to about 40 wt. -% with respect to the whole composition.

The nature of the di- or trivalent ion source is not particularly limited. In principle any di- or trivalent ion source can be used which is able to form a temporary complex with the alginate. Ions forming irreversible complexes with the alginates are not preferred. Divalent ions which can be used are e.g. calcium ions, barium ions, copper ions or aluminum ions.

The nature of the counter ion is not particularly limited, either. Counter ions found to be useful include phosphate, hydrogenphosphate, sulfate, carbonate, chloride, bromide, oxalate, acetate, succinate or fluoride. The di- or trivalent ion source may contain in addition crystal water.

From the divalent ions calcium ions are preferred. A preferred source of calcium ions includes calcium hydrogenphosphate like calcium hydrogenphosphate dihydrate or calcium pyrophosphate. Other calcium sources which can be used include calcium sulfate, calcium carbonate, calcium chloride, calcium oxalate or complexes of calcium with EDTA. Barium carbonate or copper(II) carbonate in which crystal water might be incorporated are also useful divalent ion sources. A particular ion source can be used alone or in combination with other ion sources.

The curable pastes of the invention comprise water in an amount sufficient to form an aqueous gel with the alginate powder. However, compared to alginate impression materials which usually contain water in an amount of about 60 wt. -% or higher, the amount of water in the inventive composition is typically comparable low. An amount of less than about 60 wt. -% or less than about 55 wt. -% or less than about 50 wt. -% with respect to the whole composition was found to be suitable. No particular minimum amount of water is needed, however, the composition can comprise water in an amount of at least about 10 or at least about 20 or at least about 30 wt. -% with respect to the whole composition. Examples of ranges which have been found to be useful include ranges from about 20 to about 60 or from about 30 to about 50 wt. -% water with respect to the whole composition.

The curable composition can contain a filler, however, a filler is not mandatory and thus might not be present at all. If a filler is present, it is typically present in an amount of less than about 30 wt. -% or less than about 20 wt. -% or less than about 10 wt. -%. In certain embodiments, the filler can be present in an amount of from 0 to about 25 wt. -%. The filler can be present in an amount of 1 to about 30 wt. -% or in a mount of about 5 to about 15 wt. -%.

A wide variety of inorganic, especially hydrophobic fillers may be employed such as silicas, aluminas, magnesias, titanias, inorganic salts, metallic oxides and glasses. It has been found to be possible to employ mixtures of silicone dioxides, including those derived form crystalline silicon dioxide, such as pulverized quartz (particle size: about 4 to about 6 μm); amorphous silicone dioxides, such as a diatomaceous earth (particle size: about 4 to about 7 μm); and silanated fumed silica, such as Cab-o-Sil TS-530 (160-240 m$^2$/g), manufactured by Cabot Corporation. Varying the sizes and surface areas of the foregoing materials enables one of the cured compositions. Some or all of the foregoing hydrophobic fillers may be surface treated with one or more silanating agents, as known to those of ordinary skill in the art. Such a silanation may be accomplished, e.g., using known halogenated silanes or silazides. Some useful functionalized silicas are commercially available, e.g., products sold under the brands Aerosil™ (Degussa) or HDKH™ (Wacker).

Examples of typical fillers which can be used are non-reinforcing fillers including quartz, cristobalite, calcium silicate, diatomaceous earth, zirconium silicate, wollastonite (e.g. Tremin™) montmorillonite such as bentonite, zeolite, including molecular sieves such as sodium aluminium silicate, metal oxide powder such as aluminium or zinc oxide or their mixed oxides, barium sulphate, calcium carbonate, plaster, glass and plastic powder. The fillers can be surface treated. The surface treatment can generally be carried out with the same methods as described for reinforcing fillers.

Suitable fillers also include reinforcing fillers such as e.g. pyrogenic or precipitated silicic acid and silica aluminium mixed oxides. The above mentioned fillers can be hydrophobized as well e.g. by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than about 50 μm.

In another embodiment the composition might contain a further network builder to enhance mechanical strength, if needed. The additional network(s) may be built by tailor-made organic or other natural compound(s) like polyethers, polyether derivatives, polyvinyl alcohol derivatives, polyrotaxane derivatives, cellulose derivatives, chitosoane derivatives, cyclodextrine derivatives, hyaluronic acid derivatives, polyacrylamides, polyacrylamide derivatives, polymethylacrvlamides, polylacrylamide derivatives and mixtures thereof.

A network builder might not be present at all, but can be present in an amount up to about 25 wt. -% or up to about 50 wt. -% with respect to the whole composition. If a network builder is present, it is typically present in an amount of at least about 3 wt. -% or at least about 10 wt. -% with respect to the whole composition.

The curable composition also contains a retarder. The manner how the availability and/or concentration of cations (charge: 2+ and/or 3+) being able to react or interact with the alginate is controlled or achieved may have an influence of the curing speed, the gelation kinetics and/or on physical properties of the cured composition like tensile strength or the shear storus modulus value G'.

In a preferred embodiment, the retarder can undergo a change in the chemical structure such as a ring-opening of a cyclic structure in an acidic environment. Agents with a cyclic structure may contain ester or urethane units. The ring itself is usually comprised of five or six atoms such as carbon, oxygen or nitrogen atoms.

A particularly preferred embodiment of a retarder for the inventive composition comprises a D-glucono-δ-lactone structure. The D-glucono-δ-lactone can contain further substituents, like C1 to C3 alkyl groups or halogen atoms. If the D-glucono-δ-lactone used contains substituents, these substituents should preferably not negatively influence the reactivity of the D-glucono-δ-lactone under the conditions the composition of the present invention is used.

Alternatively or in addition to components containing a D-glucono-δ-lactone structure, inorganic phosphates, water-soluble phosphates, or organic acids like citric acid or EDTA may be used. These substances may also function as retarder. The organic acids may be present as salts. The inorganic phosphates and the salts of the organic acids may have alkali or ammonium cations as counter ions.

The amount of the retarder to be used is not particularly limited as long as the intended needs in the dental field can be met. Typically the agent is used in an amount of at least about 5 wt. -% or of at least about 10 wt. -% or of at least about 15 wt. -%. The agent can be used up to an amount of about 50 wt. -% or up to an amount of about 40 wt. -% or up to an amount of 20 wt. -%. Thus, typical ranges for the amount of the amount of the above mentioned agent include ranges from about 5 to about 50 wt. -%, or from about 10 to about 40 or from about 15 to about 30 wt. -% with respect to the whole composition.

For the dentist it is sometimes important that the curable composition has a reasonable working time. Thus, the curable composition should have a curing or setting behavior which enables the practitioner to use the composition in the daily practice.

It has been found that the curing behavior of a preferred inventive composition essentially follows a sigmoid function, that is a mathematical function that produces a sigmoid curve which is a curve having an "S" shape. After mixing the components, the viscosity of the composition is still low since the curing reaction has not fully started. During this "delay time", the composition can easily be applied and the shape of the composition modified according to the dentists needed. After this phase, the curing reaction starts more rapidly and reaches a plateau. The upper limit of the plateau reflects the shear storus modulus value $G'_{max}$.

In certain embodiments, curing of the composition follows a sigmoidal function at a time from about 30 s to about 15 min after the start of the mixing of the components of the curable compositions.

It has been found that a curable past showing a shear storus modulus value $G'_{max}$ of at least 150,000 Pa, if measured with a dynamic stress rheometer equipped with a 15 mm parallel plate geometry with grooved surfaces and a measurement gap of 1 mm at 36° C., is suitable to fulfill the dentists needs. This value is preferably reached within about 15 min after end of mixing.

In another embodiment the G'-value determined 1 min after end of mixing the composition should be less than about 5 or about 10% of the maximal measurable value of G' ($G'_{max}$) if measured for about 15 min at 36 ° C.

In a further embodiment, the composition cures in a reasonable period of time which allows a dental application. E.g., after 10 min at 36° C. the measured value for G' is at least about 65% of $G'_{max}$ or at least about 75% of $G'_{max}$.($G'_{max}$ measured within 15 min after end of mixing).

Typically, the curable composition cures at 36° C. within 15 about min or within about 10 min or within about 7 min after mixing the components.

Moreover, it has been found that depending on the formulation chosen, the inventive curable composition has good mechanical properties such as tensile strength and/or elongation at break values.

In one embodiment the cured composition shows a tensile strength of at least about 0.4 MPa or of at least about 0.5 MPa or of at least about 0.6 MPa measured according to "Measurement of tensile strength and elongation at break" described in the examples hereinafter.

In another embodiment the cured composition shows an elongation at break value of at least about 70% or of at least about 80% or of at least about 100% measured according to "Measurement of tensile strength and elongation at break" described in the examples hereinafter.

In a further embodiment, the inventive composition retraction device has a colour being different from red or white. This allows an easy detection in the patient's mouth (especially from oral tissue and/or tooth structure) and control if after the treatment all residues of the retraction device have been removed from the sulcus. E.g., a blue, green or violet colour was found suitable. Colouring of the composition can be achieved by incorporating colorants or pigments (organic and inorganic) into the composition.

In a further embodiment the composition can comprise one or more haemostatic agents. Haemostatic agents (sometimes also referred to as adstringent agents) that may be useful in assisting haemostasis include, but are not limited to aluminum compounds such as potassium aluminum sulfate, aluminum ammonium sulfate, aluminum sulfate, aluminum chlorohydrate, aluminum acetate, other water soluble astringent aluminum salts, and mixtures thereof. Another class of astringent agents includes iron-based compositions such as ferric salts, including but not limited to ferric sulfate, ferric subsulfate, ferric chloride, and mixtures thereof. Other astringents include permanganates and zinc chloride. Also organic haemostatic agents may be used like tannines, adrenaline or 8-hydroxyquinoline derivatives. Preferred haemostatic agents are aluminum compounds.

In another embodiment, the curable composition can comprise an anti-microbial agent. This might help reducing health risks for professionals in the dental offices and laboratories as well as for patients caused by bleeding prior impression taking caused by drilling or retracting the gingival cuff. It may reduce the risk of contamination of the patient having a wound as well as the risk of contamination of the impression taken, thus preventing contamination of dental professionals in the dental office as well as of the dental lab.

To provide an efficient and time-saving solution the curable composition can contain the anti-microbial component when delivered to the dentist. The composition can also contain an adstringent agent in addition.

It is known that some haemostatics which are used in solution or together with retraction cords (the cords may be impregnated or soaked in solution prior use) can compromise the setting reaction of certain impression materials.

For instance, as indicated in the instruction of use of certain 3M ESPE polyether impression materials epinephrine (adrenaline), 8-hydroxyquinoline sulfate or iron (III) sulfate may impair the setting behaviour.

Thus, it can be beneficial, if residues of the composition, which were left in the sulcus by accident do not interfere with or negatively affect the setting reaction of the impression material used after the retraction procedure. Therefore, it can be an advantage, if the anti-microbial agent used is compatible with the impression material and does not compromise the setting behaviour thereof.

Anti-microbial agents which may be used in combination with the curable composition include amino group containing organic anti-microbial agents, halogen containing organic anti-microbial agents, cationic surfactants, mono- and polyhydric phenols, anti-microbial peptides, bactericins, antibiotics, aldehydes p-hydroxy benzoates or parabenes, lauricidin, enzymes, proteins, fluoride, EDTA or natural oils with antimicrobial properties.

Furthermore, it can be advantageous to use combinations of anti-microbial compounds to generate and additive or synergistic effect.

Useful combinations include chlorhexidine or derivatives thereof and aldehydes (glutaraldyde, phtaldehyde) and chlorhexidine or its derivatives and salts of phenolics or acids. It can also be preferred to use acid adducts of chlorhexidine or its derivatives like e.g., acetates, chlorides, nitrates, sulfates or carbonates.

Chlorhexidine and its derivatives (hereinafter referred to as CHX) are commercially available in water-based solutions (e.g. a 20% aqueous solution of CHX diguconate, CAS 18472-51-0) or as a pure compound or as a salt. As additive to non-water based impression materials the pure compound (CAS 55-56-1) and CHX salts like CHX diacatate monohydrate (CAS 56-95-1) or CHX dihydrochloride (CAS 3697-42-5) are preferred.

CHX also seems to be especially suited as an additive due in part to its well-known and proven anti-microbial action against Gram positive and Gram negative microorganisms including the oral Streptococci and Lactobacilli. CHX is bacteriostatic for *Mycrobaterium*. CHX is also active against yeasts including *Candida albicans* and viruses including HIV, HBV, HCV, Influenza- and Herpes virus. A further advantage of CHX is its low toxicity.

Preferred anti-microbial agents include: Hexitidin, Cetypyridinimucloride (CPC), Chlorhexidin (CHX), Triclosan, Stannous Chloride, Benzalkonium Chloride, non-ionic or ionic surfactants (e.g. quaternary ammonium compounds), alcohols [monomeric, polymeric, mono-alcohols, poly-alcohols (e.g. Xylitol, Sorbitol), aromatic (e.g. phenol)], antimicrobial peptides (e.g. histatins), bactericins (e.g. nisin), antibiotics (e.g. tetracycline), aldehydes (e.g. glutaraldehyde) inorganic and organic acids (e.g. benzoic acid, salicylic acid, fatty acids) or there salts, derivative of such acids such as esters (e.g. p-hydroxy benzoate or other parabenes, lauricidin), enzymes (e.g. lysozyme, oxidases), proteins (e.g. enamel matrix protein, prolin rich proteins), fluoride, EDTA, essential oils (e.g. thymol).

An example of a useful combination of anti-microbial agent and adstringent agent is aluminium chloride or partially neutralized aluminium chloride and CHX dichloride.

In another embodiment a vasoconstrictor such as epinephrine and/or propylhexedrine can be added.

Thus, the inventive composition may also contain further additives like pigment(s), dye(s), flavouring(s), adstringent (s), haemostatic agents and/or anti-microbial agents.

These agents can be incorporated in the curable composition. Typically, those agents or additives can be present in an amount of about 0.01 wt. -% to about 10 wt. -% or of about 0.02 wt. -% to about 7 wt. -% with respect to the whole composition.

The curable composition should preferably be made of or comprise only non-toxic substances. A substance is classified as non-toxic, if its intended use does not negatively affect the patient's health.

The invention is also directed to a kit of parts for producing a composition for retracting ginigva from a tooth structure comprising part I and part II, wherein part I comprises water and part II comprises the retarder. The other components of the composition can either be present in part I or in part II or in part I and part II.

The state of aggregation of the parts of the kit is not particularly limited. The individual parts may be predominantly present in solid, powder, pasty or liquid state. If part II is a powder, the powder may contain besides the retarder, the polymeric organic molecules the hydrogel is made of, that is the alginate. In other embodiment, part I of the kit comprises the alginate, the retarder and the di- or trivalent ion source. Part I of the kit may contain all components that are present in the formulation except for water.

In a further embodiment the invention is directed to a kit of parts comprising a curable composition as defined in the text and a curable impression material, the setting behaviour of which is not negatively affected if cured in the presence of the retraction device.

The impression materials which can be used in combination with retraction devices are not particularly limited in regard to their chemistry and nature. Polyether moieties or silicone moieties containing impression materials have been found to be useful. In a preferred embodiment, the cured composition becomes part of the impression material to be applied after the retraction procedure. This saves time for the dentist and there is no need to remove the cured paste from the sulcus anymore.

Examples of polyether moieties containing impression materials are given in U.S. Pat. No. 6,383,279 (3M ESPE), US 2002/0156149 (HeraeusKulzer) and US 2005/0250871 (Bublewitz). Commercially available materials are sold e.g. under the brand Impregum™ (3M ESPE).

The kit can further comprise accessories like retraction caps. Retraction caps can be useful for keeping the retraction device in place until an impression is taken. Retraction caps can be made of soft, tissue friendly material, e.g. cotton. However, other materials might be useful as well. If appropriate a temporary restauration can be used as retraction cap, too. Commercially available retraction caps are e.g. sold under the brand Comprecap™ (Coltène Whaledent).

The invention is also directed to a method of using a component comprising a D-glucono-δ-lactone structure and its derivatives for producing a curable dental retraction composition. This particular component (D-glucono-δ-lactone) and its derivatives were found to be useful for adjusting the curing behaviour and for providing a dental retraction composition having an appropriate working time, preferably in combination with sufficient mechanical properties.

A possible method of using the composition of the invention in the dental practice comprises the steps of a) providing the curable composition and b) applying the composition to a tooth structure. Further steps can be: c) allowing the curable composition to cure and d) removing the curable composition after curing from the sulcus and/or e) making an impression of the tooth structure, the sulcus of which has been widened by the curable composition. Thus, a method of the invention can involve a method of retracting the gingiva of a prepared tooth.

In FIGS. 1 and 2 the application procedure is exemplified. After mixing the components, the curable composition (1) is dispensed out of a nozzle (2) of a capsule or cartridge (3) into the sulcus (4) of a tooth structure (5). The composition is left to harden for about 4 min. After hardening, the cured composition may be pushed deeper into the sulcus with the aid of a dental instrument (not show). After sufficient retraction and after sufficient hemostasis has been achieved, the cured composition (1) can be removed from the sulcus (4) like a cord using an application instrument (6) such as a pincer. As show in FIG. 2, the sulcus has been widened due to the application of the inventive retraction composition compared to the sulcus before the application. After removal of the cured composition an impression-taking process with a common impression material can follow (not shown).

What can be seen is, that the curable composition can be fast and easily applied to the sulcus and removed after curing therefrom, preferably in one piece. Due to biocompatible and non sticky surface properties of the alginate containing composition, it does not adhere to the tissue of the sulcus or the prepared tooth structure.

Thus, the invention also relates to a device for mixing and delivering the curable paste as described in the text above, the device comprising two compartments A and B, wherein compartment A comprises water and compartment B comprises the retarder, the device having the shape of a capsule or cartridge preferably with a nozzle or application tip. Alternatively, the device comprises two compartments A and B, wherein compartment A comprises water and compartment B comprises the divalent ion source, the device having the shape of a capsule or cartridge with a nozzle or a cannula.

Capsules which can be used are described e.g. in U.S. Pat. No. 4,674,661 or U.S. Pat. No. 6,715,645. Containers which may be used are described in e.g. EP 1 577 227 A1, WO 2005/118154 A1, WO 2005/016170 A1, WO 2005/016783 A1, WO 2005/094714 A, WO 2005/084819 A1 and EP Application No. 05 019 024. Those devices are usually made by injection molding and have at least two compartments. The volume which can be mixed and delivered is usually the range of up to about 2 or up to about 1.5 ml. An application tip which can be used especially in the combination with capsules is described in EP patent application No. 05014393.2. The content of the patents and applications mentioned above with regard to the description of capsules, containers and application devices is considered part of the invention and is incorporated by reference.

If the curable composition is made of a powder and a liquid, the paste may be made by hand mixing. However, mixing can also be effected using a mixing device as described in U.S. Pat. No. 5,167,448 or U.S. Pat. No. 4,890,931. Those devices are commercially available under the brands Rotomix™ and Capmix™ (3M ESPE). Also mixing devices for mixing amalgam can be used.

The invention is hereinafter described by examples, the description of which is not intended to limit the scope of the invention.

EXAMPLES

If not reported otherwise, all tests were conducted at ambient conditions (23° C.; 50% humidity and room pressure). The following substances were used (Table 1):

TABLE 1

| | |
|---|---|
| Alginate 1 | "Protanal KF 200S", Fa. FMC Biopolymers (potassium salt with guluronic content of about 65% and a particle size of about 75 μm) |
| Alginate 2 | "Protanal HF 120 RBS", Fa. FMC Biopolymers (sodium salt with guluronic content of about 45 to 55% and a particle size of about 75 μm) |
| D-glucono-δ-lactone (CAS-No. 90-80-2) | available from Sigma |
| Ca(HPO$_4$) * 2 H$_2$O (CAS-No. 7789-77-7) | available from Aldrich |

Example 1

Reference 10.0% Protanal HF 120 RBS (Alginate 2)
20.0% Ca(HPO$_4$)*2H$_2$O
20.0% D-glucono-δ-lactone
50.0% deionized water Example 2

Invention 10.0% Protanal KF 200S (Alginate 1)
20.0% Ca(HPO$_4$)*2H$_2$O
20.0% D-glucono-δ-lactone
50.0% deionized water Example 3

Invention 8.0% Protanal KF 200S (Alginate 1)
22.0% Ca(HPO$_4$)*2H$_2$O
30.0% D-glucono-δ-lactone
40.0% deionized water Example 4

Invention 5.0% Protanal KF 200S (Alginate 1)
25.0% Ca(HPO$_4$)*2H$_2$O
30.0% D-glucono-δ-lactone
40.0% deionized water Example 5

Reference 8.0% Protanal KF 200S (Alginate 1)
22.0% Ca(HPO$_4$)*2H$_2$O
10.0% D-glucono-δ-lactone
60.0% deionized water Rheological Measurements Measuring of the Setting Behaviour The components mentioned above were mixed and the setting behaviour of the individual compositions was investigated using commonly available oscillating rheometer. All tests were preformed at 36° C. using a dynamic stress rheometer (Physica MCR300, Anton Paar) equipped with a 15-mm parallel plate geometry with grooved surfaces (PP15-SN5326). The temperature was controlled within 0.1° C. by a Peltier element in the lower plate. The measurement gap was constant 1 mm. Dynamic strain sweep tests were preformed at a frequency of 1 s$^{-1}$ and dynamic frequency sweep tests at a strain amplitude of 0.01%. Every second a measurement point was recorded. Data was recorded over a period of time of 15.36 minutes.

The following values of G' (shear storus modulus) value were determined:

Example 1

Reference $G'_{max.}$=145 kPa
G'(10 min)=143 kPa (99% of G' max)
G' (1 min.)=32 kPa (22% of G' max)

Example 2

Invention $G'_{max.}$=351 kPa (no increase of G' was observed at a time >15 minutes)
G' (10 min)=285 kPa (81.2% of G' max)
G' (1 min.)=13 kPa (3.5% of G' max)

Example 3

Invention $G'_{max.}$=351 kPa (no increase of G' was observed at a time >15 minutes)
G' (10 min)=333 kPa (94.9% of G' max)
G'(1 min.)=13 kPa (3.7% of G' max)

Example 4

Invention $G'_{max.}$=332 kPa (no increase of G' was observed at a time >15 minutes)
G' (10 min.)=296 kPa (89.2% of G' max)
G' (1 min.)=6 kPa (1.8% of G' max)

Example 5

Reference $G'_{max.}$=139 kPa (observed after 15.36 minutes further increase of G' was observed at a time >15 minutes)
G' (10 min.)=65 kPa (46.8% of G' max)
G' (1 min.)=3 kPa (2.2% of G' max)

The curing behaviour of the examples and G' values measured are show in FIG. 3. The curing behaviour essentially follows the function G' (t)=1/(1+e$^{-1}$)

Measurement of Tensile Strength and Elongation at Break

Square profile specimens (2×2 mm) with 14 mm parallel edges were tested in a universal testing machine (UPM Z020, Zwick). The specimens were allowed to cure for 10 minutes at 23° C. at 50% relative humidity before testing. The test velocity was 50 mm/min and the force sensor was calibrated up to 500 N. Tensile strength and elongation at break values were determined The test results are given in Table 2.

TABLE 2

| | | property tensile test | |
|---|---|---|---|
| | unit | tensile Strength MPa | elongation % |
| Example 1 (reference) | | not measurable * | not measurable * |
| Example 2 (inventive) | | 0.7 | 128 |
| Example 3 (inventive) | | not determined | not determined |
| Example 4 (inventive) | | not determined | not determined |
| Example 5 (reference) | | not measurable * | not measurable * |

* not measurable: value to low to be determined.

The invention claimed is:

1. A curable dental retraction composition comprising:
   a. an alginate in an amount from about 4 to about 20 wt. -%,
   b. a di- and/or trivalent ion source in an amount from about 5 to about 50 wt. -%,
   c. water in an amount from about 20 to about 55 wt. -%,
   d. a retarder in an amount from about 5 to about 50 wt. -%, and
   e. a filler in an amount from 1 to about 30 wt. -%,
wherein the wt. -% are calculated with respect to the whole composition and wherein the shear storus modulus value $G'_{max}$ of the composition is at least 150,000 Pa when measured with a dynamic stress rheometer equipped with a 15 mm parallel plate geometry with grooved surfaces and a measurement gap of 1 mm at 36° C.

2. The curable composition according to claim 1, wherein the curing of the composition follows a sigmoidale function at a time from about 30 s to about 15 min after the start of the mixing of the components of the curable compositions.

3. The curable composition according to claim 1, wherein the shear storus modulus value G' measured 1 min after end of mixing of the components of the curable composition is less than about 10% of the maximum value of G'.

4. The curable composition according to claim 1, wherein the molecular weight of the alginate is in a range from about 200,000 to about 400,000 g/mol.

5. The curable composition according to claim 1, wherein the alginate is present in the curable paste in the amount of at least 5 wt. -% with respect to the whole composition.

6. The curable composition according to claim 1, wherein the alginate has a guluronate content of at least 50 wt. -% with respect to the weight of the alginate in dry form.

7. The curable composition according to claim 1, wherein the alginate is selected from the group consisting of *Laminaria hyperborean Stem, Laminaria hyperborean Leaf* and *Lessonia trabeculata*.

8. The curable composition according to claim 1, wherein the ion of the di- and/or trivalent ion source is selected from the group consisting of calcium, barium, aluminium and copper.

9. The curable composition according to claim 1, wherein the retarder of the composition is selected from the group consisting of water-soluble phosphates, inorganic phosphates, citric acid, citric acid salts, and substances comprising a D-glucono-δ-lactone structure.

10. The curable composition according to claim 1, further comprising one or more network building component(s) selected from the group of polyethers, polyether derivatives, polyvinyl alcohol derivatives, polyrotaxane derivatives, cellulose derivatives, chitosoane derivatives, cyclodextrine derivatives, hyaluronic acid derivatives, polyacrylamides, polyacrylamide derivatives, polymethylacrylamides, polymethylacrylamide derivatives and mixtures thereof.

11. The curable composition according to claim 1, further comprising one or more additives selected from the group consisting of filler(s), pigment(s), dye(s), flavouring(s), adstringent(s), haemostatic agents and mixtures thereof.

12. The curable composition according to claim 1, wherein the composition has at least one of the following properties:
   a. a tensile strength of at least 0.5 MPa, or
   b. an elongation at break of at least 70%.

13. A kit of parts for producing the curable dental retraction composition of claim 1, wherein the kit comprises:
   a. a part I comprising water and
   b. a part II comprising the retarder,
   wherein the other components of the composition are either present in part I or in part II or in both part I and part II.

14. A device for mixing and delivering the curable dental retraction composition of claim 1, the device comprising two compartments A and B, wherein compartment A comprises water and compartment B comprises the di- and/or trivalent ion source, the device having the shape of a capsule or cartridge with a nozzle or a cannula.

15. A method of retracting the gingiva of a prepared tooth, the method comprising the steps of a) providing a curable dental retraction composition, and b) applying the curable composition to the sulcus of the prepared tooth; wherein the curable dental retraction composition comprises:
   a. an alginate,
   b. a di- and/or trivalent ion source,
   c. water in an amount less than about 60 wt. -%,
   d. a retarder, and
   e. a filler in an amount less than about 30 wt. -%,
wherein the wt. -% are calculated with respect to the whole composition and wherein the shear storus modulus value $G'_{max}$ of the composition is at least 150,000 Pa when measured with a dynamic stress rheometer equipped with a 15 mm parallel plate geometry with grooved surfaces and a measurement gap of 1 mm at 36° C.

* * * * *

UNITED STATES PATENT AND TRADEMARK OFFICE
CERTIFICATE OF CORRECTION

| | |
|---|---|
| PATENT NO. | : 8,142,562 B2 |
| APPLICATION NO. | : 12/376527 |
| DATED | : March 27, 2012 |
| INVENTOR(S) | : Thomas Klettke |

It is certified that error appears in the above-identified patent and that said Letters Patent is hereby corrected as shown below:

Column 1
Line 43            Delete "adstingent(s)" and insert -- adstringent(s) --, therefor.

Column 2
Line 54            Delete "ginigva" and insert -- gingiva --, therefor.

Column 4
Line 56            Delete "haemostic" and insert -- haemostatic --, therefor.

Column 5
Line 27            Delete "non-hydrophilc" and insert -- non-hydrophilic --, therefor.

Column 7
Line 33            Delete "form" and insert -- from --, therefor.

Column 8
Line 4             Delete "chitosoane" and insert -- chitosan --, therefor.
Lines 6-7          Delete "polymethylacrvlamides, polylacrylamide" and insert
                   -- polymethylacrylamides, polymethylacrylamide --, therefor.

Column 10
Line 30            Delete "bactericins," and insert -- bacteriocins, --, therefor.
Line 38            Delete "(glutaraldyde, phtaldehyde)" and insert -- (glutaraldehyde,
                   phthalaldehyde) --, therefor.
Line 45            Delete "diguconate," and insert -- digluconate, --, therefor.
Line 48            Delete "diacatate" and insert -- diacetate --, therefor.
Line 55            Delete "Mycrobaterium." and insert -- Mycobacterium. --, therefor.
Lines 59-60        Delete "Hexitidin, Cetypyridinimucloride" and insert -- Hexetidine,
                   Cetylpyridiniumchloride --, therefor.

Signed and Sealed this
Sixth Day of November, 2012

David J. Kappos
*Director of the United States Patent and Trademark Office*

CERTIFICATE OF CORRECTION (continued)
U.S. Pat. No. 8,142,562 B2

Column 10 (continued)
Line 60                       Delete "Chlorhexidin" and insert -- Chlorhexidine --, therefor.
Line 65                       Delete "bactericins" and insert -- bacteriocins --, therefor.

Column 11
Line 24                       Delete "ginigva" and insert -- gingiva --, therefor.

Column 14
Line 66                       After "$1/(1+e^{-1})$" insert -- . --.

Column 16
Line 17                       In Claim 10, delete "chitosoane" and insert -- chitosan --, therefor.